(12) United States Patent
Bohnenkamp

(10) Patent No.: US 6,252,657 B1
(45) Date of Patent: Jun. 26, 2001

(54) REFLECTION FLUOROMETER

(76) Inventor: Wolfram Bohnenkamp, Thingolstrasse 24, 78465 Konstanz (DE)

( * ) Notice: Subject to any disclaimer, the term of this patent is extended or adjusted under 35 U.S.C. 154(b) by 0 days.

(21) Appl. No.: 09/133,511

(22) Filed: Aug. 12, 1998

(30) Foreign Application Priority Data

Aug. 13, 1997 (DE) ............................................ 197 35 144

(51) Int. Cl.⁷ ............................ G01N 21/01; G01T 1/161
(52) U.S. Cl. ............................................ 356/244; 250/302
(58) Field of Search ............................. 356/318, 300, 356/317, 445, 446, 417, 244; 250/302, 432 R, 461.2, 373

(56) References Cited

U.S. PATENT DOCUMENTS

| 4,716,121 | 12/1987 | Block et al. |
| 5,221,958 | * 6/1993 | Bohnenkamp ............... 356/318 |

FOREIGN PATENT DOCUMENTS

| 41 526 | 2/1986 | (AT) . |
| 35 32 563 C2 | 3/1986 | (DE) . |
| 36 30 351 A1 | 3/1987 | (DE) . |
| 42 27 678 A1 | 2/1994 | (DE) . |
| 43 08 202 C2 | 9/1994 | (DE) . |
| 0 470 982 B1 | 7/1993 | (EP) . |
| WO 93/18405 | 9/1993 | (WO) . |

OTHER PUBLICATIONS

Capillary waveguide sensors, Otto S. Wolfbeis, Trends in analytical chemistry, vol. 15, No. 6, 1996, pp. 225–232.
Fiber–Optic Chemical Censors for Competitive Binding Fluoroimmunoassay, Bruce J. Tromberg and Michael J. Sepaniak, Analytical Chemistry, vol. 59, No. 8, Apr. 15, 1987, pp. 1226–1230.

* cited by examiner

Primary Examiner—Frank G. Font
Assistant Examiner—Roy M. Punnoose
(74) Attorney, Agent, or Firm—Barnes & Thornburg

(57) ABSTRACT

A reflection fluorometer comprises a light guiding capillary with a fluorescent coating of the inner wall side, and a light source for excitation. The light source is positioned so that the light meets the outer longitudinal side of the capillary and part of the light penetrates the capillary. At least one sensor is positioned for sensing light at the front end of said capillary to measure the fluorescent light which leaves the capillary on that end. The capillary is constructed from light guiding material for the light that is excited in the area of the evanescent field, and the refractive index of an inner coating on the capillary is smaller than the refractive index of the capillary material.

20 Claims, 3 Drawing Sheets

REFLECTION FLUOROMETER

TECHNICAL FIELD

The present invention relates to a reflection fluorometer having a capillary as a light guiding device. The inner wall side of it is sensitized to retain different analytes. Using fluorescent signals renders it possible to measure the concentrations of different analytes with at least one light sensor at the end of that capillary.

BACKGROUND

It is known that light which impinges on the interface of two media with different refractive indices at a certain angle will be totally reflected if the angle of incidence is larger than the critical angle $\Theta_c$. But if light is excited in the boundary layer, the evanescent wave area, of the medium with the lower refractive index, it can enter the medium with the larger refractive index even if the angle of incidence is greater than $\Theta_c$.

An appropriate system is described in WO 93/18405. The exciting light is guided by a transparent solid onto a cuvette and the fluorescent light from the evanescent field enters the light guiding device and is directed to the detector by a inclined area. This arrangement has the weakness that only a small proportion of the excited light enters the sensitive system and therefore the sensitivity of that system is relatively small.

In U.S. Pat. No. 4,716,121 an arrangement for fluorescent measurements is described especially for immunoassays. In this reference a light guiding rod is used, which is enclosed in a floating chamber for the perfusion with the probe fluid. The exciting light is coupled into the front end and therefore the density of the energy is small and also the signal of the fluorescent light, which is measured at the same end using a dichroic mirror.

In a comparable technique the reflection fluorometer works, which is described in EP 0 470 982. In this reference also the exciting light is coupled into the front end and the fluorescent light is measured at the same end. Therefore the identical restrictions apply as in U.S. Pat. No. 4,716,121.

DISCLOSURE OF THE INVENTION

This invention seeks to use fluorescent light with a greater efficiency and therefore also sensitivity to low concentrations of different analytes. Illustrative embodiments and useful implementations of this invention follow.

Elements of the reflection fluorometer are the light guiding capillary which will receive one or more different analytes for complexation at the inner wall of that capillary. The concentrations of the one or more analytes are measured at one end of the capillary with a light sensitive instrument. The excitation of the fluorescence takes place with a light in the transverse direction of the capillary. The light guiding material therefore is constructed using substances which are transparent to the exciting and fluorescent emitted light. It also should be transparent for light in the infrared region, if fluorescent dyes in that region are used.

It is advantageous to use prismatic optics to guide the light from the source to the capillary. An illustrative embodiment uses a wedge shape with a trapezoidal cross-section. The optical design should be characterized in that the relevant angles and the refractive index of the wedge are chosen so that the light is emitted only at the small side which is close to the capillary. That means the light from the source is reflected up to many times from the outer walls of that wedge until it enters the capillary. If the irradiation enters the wedge with too great an angle or if the reflection index of its material is too high, it is possible that the light will leave the wedge on the entrance or side area. The wedge may also have direct contact to the capillary.

The fluorescent light from the end of the capillary may be guided in a similar way if a charge coupled device (CCD) is used as a sensor. The wedge is positioned in front of the end of that capillary and will be focused on the entrance slit of the monochromator by lenses.

Further illustratively, a coupling device is positioned at the end of the capillary opposite the end used for filling and positioning. This also can give the advantage of the enhancement of the fluorescent light intensity on the opposite end of the capillary. Further illustratively, a lateral flap is provided on the coupling device for reproducible positioning. This helps to measure results several times in the identical rotational position. This especially is useful for kinetic determinations, where repetitive measurements are necessary.

In an illustrative reflection fluorometer the excitation light is intermittently pulsed. This allows time-resolved measurements, in which the fluorescence is measured after removal of the background noise of electronic or probe-specific interactions. Therefore the sensitivity and reproducibility of the determinations will be enhanced. Those light pulses can be produced using mechanical shutters or pulsed light sources, such as lasers or flash-lamps. The sensor can be, for example, a photomultiplier or a CCD. The former may have the better sensitivity and the latter will give the possibility of faster data handling and corrective evaluations.

If optical grids or filters are used between the capillary and the sensor, it will be possible to measure wavelength-resolved measurements. That enables the determination of multiple dyes in one probe. By combining the time- and wavelength-resolved determinations it is possible to use analytical mathematics to reach high sensitivity for a multitude of analytes.

The inventive reflection fluorometer may be optimized by the use of an additional sensor for the determination of fluctuations in the energies of the excitation light or otherwise reflected light. It also will be possible to detect positional differences of the capillary. This will help to make a mathematical compensation or corrective evaluation of the measurements. All measurement and corrective data will assembled in a computational data store and the evaluation will produce the most probable interpretations concerning the analytical and diagnostic statements.

It is advantageous to use as a light guiding device a capillary with a low ratio of inner volume to surface area of the capillary to enhance the sensitivity and the detection limits of the system. The volume to surface am relationship may be in the range of 1:3 to 1:10 $\mu l/mm^2$ and may be preferred in the range of 1:5 $\mu l/mm^2$. With this design a fivefold relationship can be reached in comparison to, for example, a microtiterwell of a 96-well plate.

With the inventional reflection fluorometer using a flash-lamp and a photomultiplier it was possible to measure a one thousand times lower concentration of fluorescein in comparison to earlier measurements well above the background, that is 1.33 pmol/l. This was measured with a signal/noise ratio of more than 2 (see FIG. 4). The border of the detection is limited by the fluorescence of the materials used for the optical design and the capillary.

In an investigation with very dissolved solutions, the inside of the capillary can be used as a concentrating unit.

The capillary is sensibilized for some elected analytes and a greater volume than the inner volume of the capillary is flowing through. In this case, it is possible to fix more analytes on the inner surface of the capillary than are present in the capillary volume. With immunoassays it is possible to overcome the Hook-effect by dilution of the sample and the concentration of the molecules in the capillary to the relevant signal height again.

It was demonstrated with avidin coated capillaries and with biotin covered microbeads that the sensitivity is quite higher in this environment. The microbeads have a diameter of 200 nm and are dyed with fluorescein. They bind to the capillary wall by the well known avidin-biotin complexation, which is very stable, and withstands multiple rinsing. With this technique it was possible to demonstrate a linear correlation of the concentration and the fluorescent signal (see FIG. 5). The coating of the capillary with avidin is done in physiological salt solution and the excess of binding areas is covered with inert proteins.

The fluorescent dyes may be bound to those microbeads or directly to biological molecules. By use of the inventive reflection fluorometer, it is possible to study antigen and antibody reactions. The binding of DNA/RNA can be measured using dyed corresponding partners as well as with intercalating dyes like Ethidium bromide. It also is possible to measure cellular compartments or even whole cells.

DETAILED DESCRIPTION OF THE DRAWINGS

The invention may be further understood by referring to the following detailed description and accompanying drawings which illustrate the invention. In the drawings.

DETAILED DESCRIPTION OF AN ILLUSTRATIVE EMBODIMENT

Figure 1:
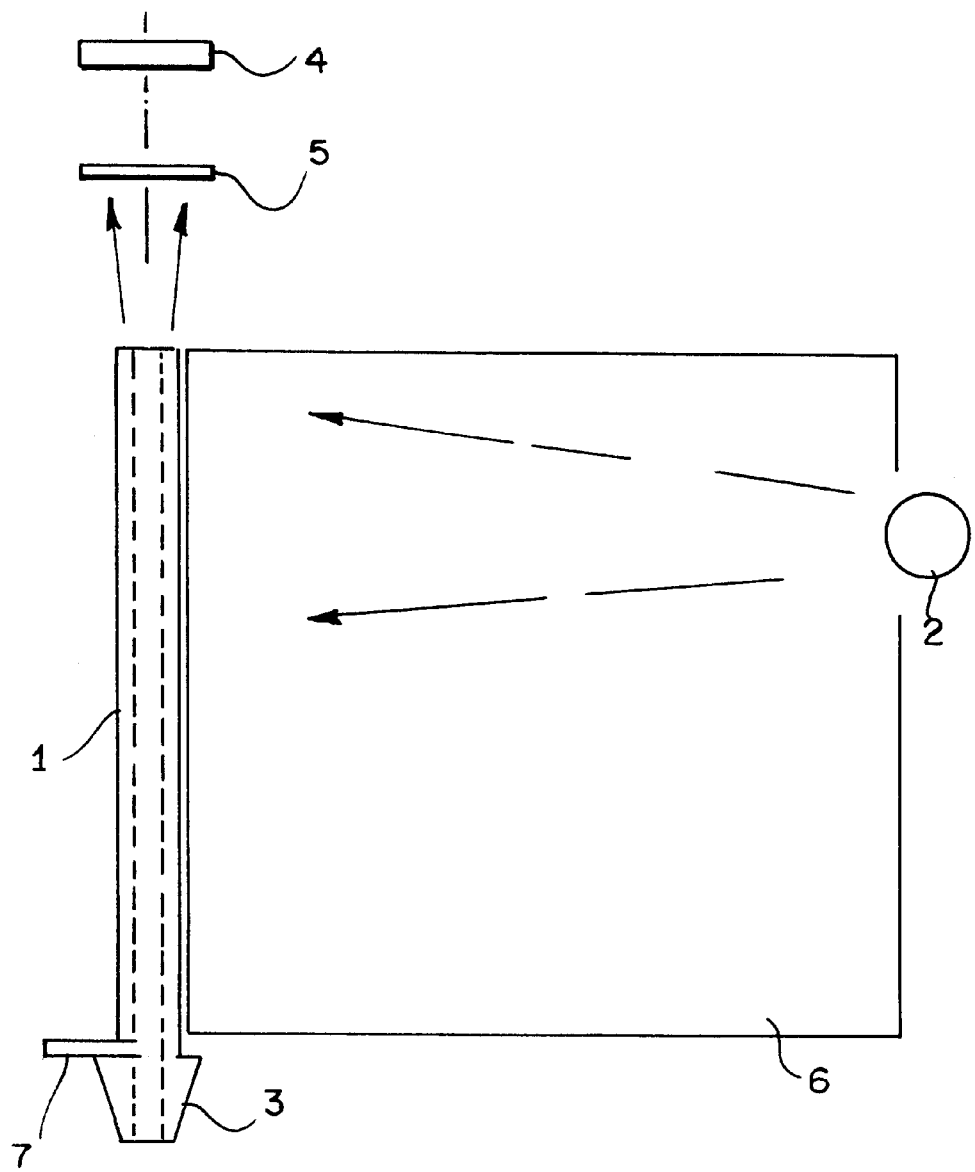
FIG. 1 illustrates a schematic longitudinal sectional view of a measuring arrangement according to the present invention.
Figure 2:
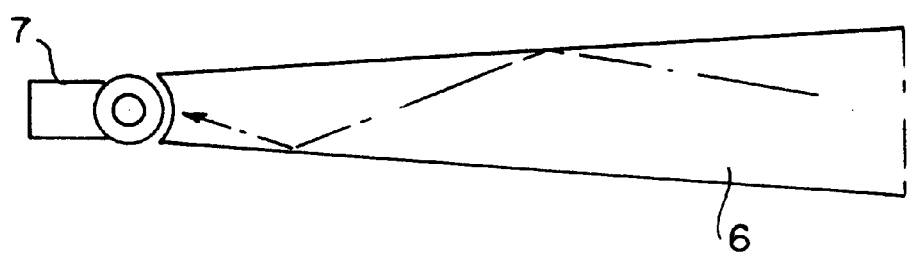
FIG. 2 illustrates a cross-section of the arrangement illustrated in FIG. 1; and, FIG. 3 illustrates a schematic of a light guiding system for guiding the fluorescent light from the capillary to the entrance slit of a monochromator.

Light from the source 2 is guided to the length of the capillary 1. The light, as indicated by arrows, reaches the light guiding capillary through an optical wedge 6. The illustrated wedge-shaped reflection-trapezoid permits almost all light from the source 2 to reach the length of the light guiding capillary 1. The geometrical dimensions and the refractive index of the material of the wedge 6 can be in close correlation. The capillary is transparent to light and contains in the inner volume at least one analyte, the concentration of which can be measured by fluorescence excitation, as is known from chemical and biochemical analytical determinations.

The fluorescent light exits the front end of the light-guiding capillary 1, as indicated by arrows, and can be measured by light sensitive instruments 4. It may be of advantage to have optical filters 5 in front of the front end of the capillary 1 to exclude unintentional light.

Figure 3:
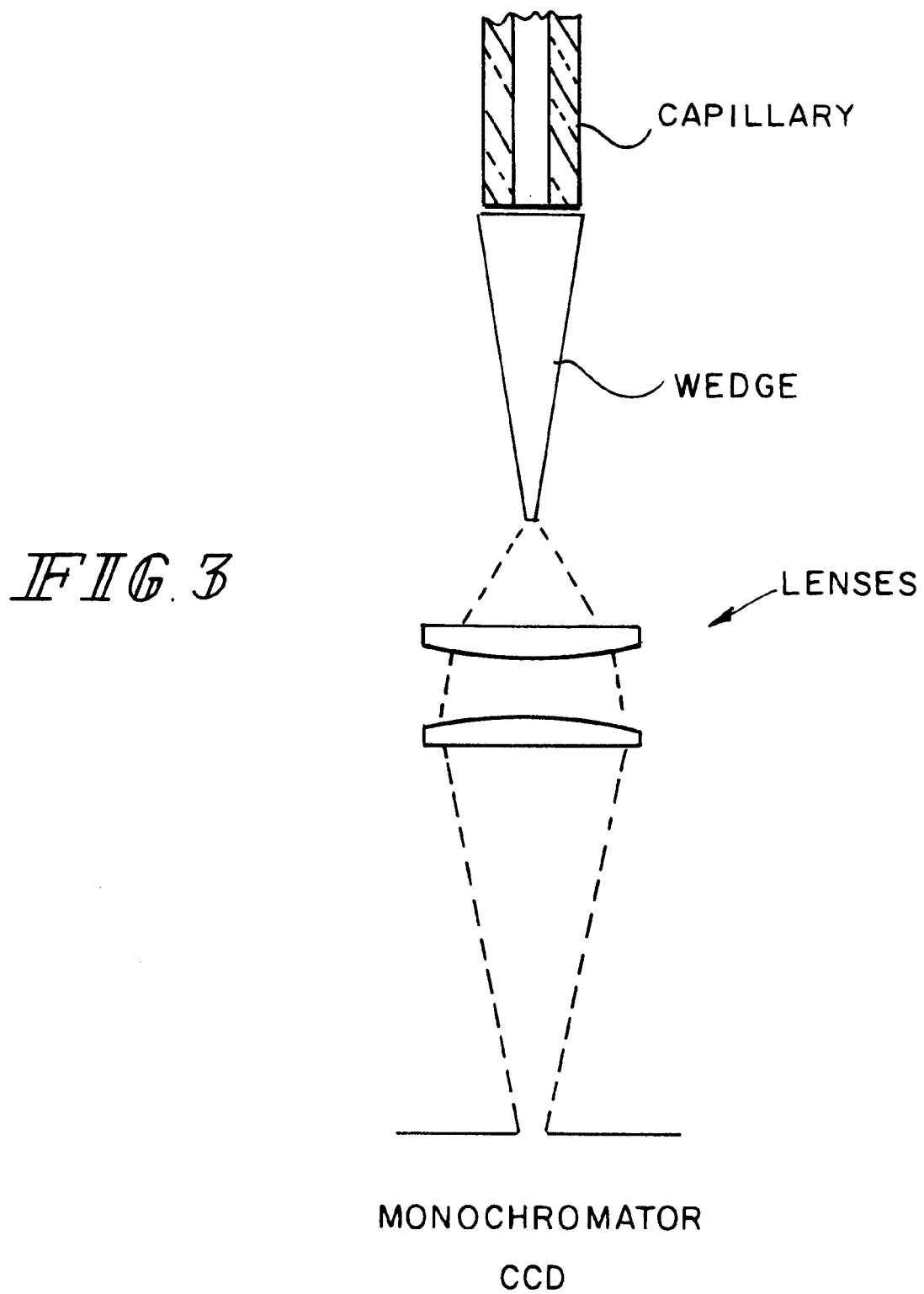
Figure 4:
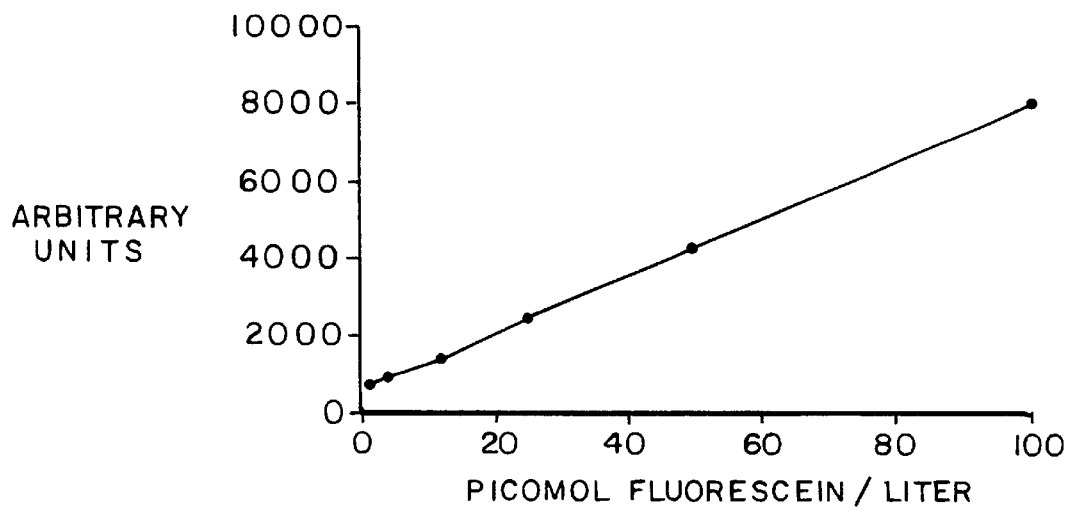
FIG. 4 illustrates concentration dependence of fluorescein in solution.
Figure 5:
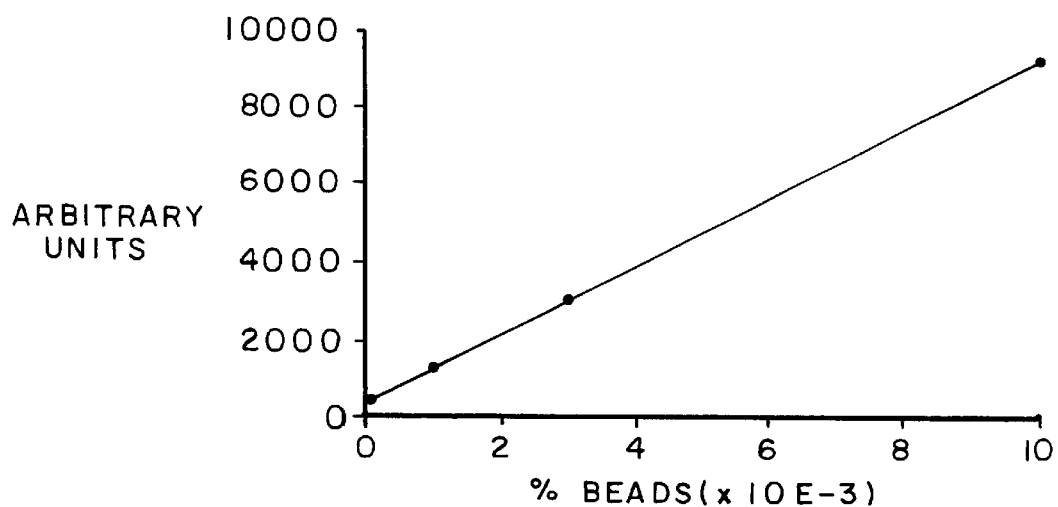
FIG. 5 illustrates the concentration dependence of bound microbeads.

Instead of filters 5, optical grids or spectrometers with CCDs can be used. In the case of CCDs, it is of advantage to use a focussing apparatus as schematically illustrated in FIG. 3. The circular cross-section of the beam of fluorescent light from the end of the capillary is changed into a thin line by a wedge-like corpus. This thin line then is focussed to the entrance cleft of a monochromator using optical lenses. This monochromator can be used in combination with a charge coupled device.

On the other side of the light guiding capillary 1, a conical end may be built. This facilitates fixing the light guiding capillary in the right position. At this side also, a lengthening piece 7 may be used to fix the light guiding capillary 1 in a definite circular position. That, in turn, eases repetitive identical positionings of the capillary.

What is claimed is:

1. A reflection fluorometer with a light guiding capillary, a fluorescent coating of the inner wall side, a light source for the excitation, which is positioned so that the light meets the outer longitudinal side of the capillary and part of the light penetrates the capillary, and at least one sensor for light at the front end of said capillary to measure the fluorescent light which leaves the capillary on that end, the capillary constructed from light guiding material for the light that is excited in the area of the evanescent field, and the refractive index of an inner coating on the capillary being smaller than the refractive index of the capillary material.

2. A reflection fluorometer according to claim 1 wherein on the opposite end of the capillary a coupling device is formed for positioning the capillary.

3. A reflection fluorometer according to claim 1 further comprising a cylindrical or prismatic optic which enables the exciting light to reach the outer side of the capillary.

4. A reflection fluorometer according to claim 1 wherein the refractive index and the shape of the excitation optic are selected so that light will only leave the optic at the opposite side to the light guiding capillary.

5. A reflection fluorometer according to claim 1 further comprising a wedge shaped reflection-trapezoid for the excitation.

6. A reflection fluorometer according to claim 1 wherein the excitation light is pulsed.

7. A reflection fluorometer according to claim 1 wherein the light sensors are photomultipliers or charge coupled devices.

8. A reflection fluorometer according to claim 1 further comprising a filter in front of the light sensor.

9. A reflection fluorometer according to claim 1 further comprising an optical grid positioned between the capillary and the sensor.

10. A reflection fluorometer according to claim 1 further comprising a cross-sectional change of the fluorescent light beam from circular to rectangular between the capillary and the entrance slit of the monochromator for the detecting unit.

11. A reflection fluorometer according to claim 1 further comprising an additional light sensor for the measurement of the excitation light and/or reflective disturbances.

12. A reflection fluorometer according to claim 1 wherein the inner volume and surface area of the light guiding capillary have a relation of 1–3 to 1–10 $\mu l/mm^2$.

13. A reflection fluorometer according to claim 1 capable of indicating more than one analyte in the capillary at the same time.

14. A reflection fluorometer according to claim 1 wherein a warping is provided at one end of the light guiding device for use in positioning.

15. A reflection fluorometer according to claim 2 further comprising a cylindrical or prismatic optic which enables the exciting light to reach the outer side of the capillary.

16. A reflection fluorometer according to claim 2 wherein the refractive index and the shape of the excitation optic are selected so that light will only leave the optic at the opposite side to the light guiding capillary.

17. A reflection fluorometer according to claim 2 further comprising a wedge shaped reflection-trapezoid for the excitation.

18. A reflection fluorometer according to claim 2 wherein the excitation light is pulsed.

19. A reflection fluorometer according to claim 2 wherein the light sensors are photomultipliers or charge coupled devices.

20. A reflection fluorometer according to claim 2 further comprising a filter in front of the light sensor.

* * * * *